United States Patent [19]

Orbach et al.

[11] Patent Number: 5,896,164
[45] Date of Patent: *Apr. 20, 1999

[54] VIDEO DISPLAY APPARATUS

[76] Inventors: Tuvi Orbach, 5 Ravenscroft Avenue, London NW11 OSA; Ernesto Marcelo Dario Korenman, ISUA, 66 Windermere Avenue, Finchley, London N3 3RA; Hugh Christopher Riddle, 3 Mulberry Court, Grand Parade, Littlestone, New Romney, Kent TN28 8LZ, all of United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/583,021

[22] PCT Filed: Jul. 20, 1994

[86] PCT No.: PCT/GB94/01571

§ 371 Date: Feb. 12, 1996

§ 102(e) Date: Feb. 12, 1996

[87] PCT Pub. No.: WO95/02989

PCT Pub. Date: Feb. 2, 1995

[30] Foreign Application Priority Data

Jul. 20, 1993 [GB] United Kingdom ............... 9315034

[51] Int. Cl.⁶ .......................... H04N 7/00; H04N 7/10
[52] U.S. Cl. ................. 348/2; 386/46; 482/902; 128/905
[58] Field of Search ................. 348/61, 65, 71, 348/74, 563, 564, 12, 13, 2, 841; 360/13, 14.1, 14.2, 14.3, 18; 358/311; 386/4, 52, 65, 46; 128/732, 905; 434/307 R, 44, 365, 247; 482/902, 7–8; 463/30, 43; H04N 7/00, 7/10

[56] References Cited

U.S. PATENT DOCUMENTS

| | | | |
|---|---|---|---|
| 2,751,583 | 6/1956 | Jones | 358/1 |
| 3,465,097 | 9/1969 | Brabon et al. | 348/722 |
| 4,064,870 | 12/1977 | Dumitrescu et al. | 128/2 |
| 4,203,130 | 5/1980 | Doumit et al. | 358/1 |
| 4,278,095 | 7/1981 | Lapeyre | 128/689 |
| 4,683,891 | 8/1987 | Cornellier et al. | 128/630 |
| 4,750,888 | 6/1988 | Allard et al. | 434/69 |
| 4,839,743 | 6/1989 | Best et al. | 434/307 R |
| 4,855,827 | 8/1989 | Best | 358/143 |
| 4,987,903 | 1/1991 | Keppal et al. | 128/732 |
| 5,131,311 | 7/1992 | Murakami et al. | 84/609 |
| 5,175,627 | 12/1992 | Josephs | 358/255 |
| 5,246,411 | 9/1993 | Rackman et al. | 482/57 |
| 5,308,296 | 5/1994 | Eckstein | 482/5 |

*Primary Examiner*—Wendy Garber
*Assistant Examiner*—Vincent Boccio
*Attorney, Agent, or Firm*—Breiner & Breiner

[57] ABSTRACT

Video display apparatus e.g. for use in biofeedback or in diagnosis is described. Between an audiovisual reproduction unit such as a video cassette player and a television display, the invention provides a signal modifying unit which can cause the television display to change. The amount of change and optionally also its type may depend on the sensing of a user parameter, for example a psychophysiological parameter of the user or patient such as electrodermal activity. The signal modification device is preferably pre-programmed and microprocessor controlled. It may also react to coded signals embedded in the composite video signal recorded on the video cassette.

11 Claims, 3 Drawing Sheets

INSERTER SECTION

VIDEO DISPLAY APPARATUS

FIELD OF THE INVENTION

This invention relates to video display apparatus and in particular to such apparatus for use in practising biofeedback techniques, in psychiatric diagnosis and in other interactive procedures.

BACKGROUND OF THE INVENTION

Biofeedback techniques for psychophysiological training have been known for some time they generally involve measuring a psychophysiological parameter of a subject to vary some sort of sense perceptible indication in dependence upon variation in the psychophysiological parameter. For example, in early biofeedback devices, the subjects were asked to look at a needle on a meter and to try and relax. By means of controlled relaxation, the meter reading could be made to change and the biofeedback in question was that the person relaxing could see that the change had actually occurred.

A wide variety of biofeedback apparatus and methods has been proposed over recent years and the sophistication of such apparatus has substantially increased. In particular, the availability of cheap computing power and the acceptability of information displayed on a computer monitor screen has led to the development and, in some cases, commercialisation of a wide variety of devices. U.S. Pat. Nos. 4,632,126, 4,683,891 and 4,800,893, as well as published International Application WO93/02622 all disclose biofeedback type apparatus including a screen which is watched by the person carrying out the biofeedback procedure. In all cases, however, the apparatus is effectively a computer driven apparatus which, in accordance with an appropriate programme, varies a computer generated screen display in an appropriate fashion dependent, in particular, on the value of a psychophysiological parameter of the user.

U.S. Pat. No. 4,149,716 discloses video game apparatus wherein in contrast to the player using a manual input to control the game, e.g. via a keyboard or joystick, the game is controlled by myoelectric impulses generated consciously by the user and detected by means of an appropriate sensor such as a headband containing contact electrodes.

U.S. Pat. No. 4,984,578, specification describes a diagnostic and treatment system for use with Alzheimer's disease. It relies on the interaction between a patient and a computer and the computer generates a display on a screen, the patient then reacting following viewing the display and thinking about it. The overall system illustrated includes a video recorder, to keep a record of the diagnostic or treatment session. The sequence of images which are displayed to the patient are generated by the computer.

U.S. Pat. No. 4,278,095 discloses a system which uses a videotape cassette player, to generate a display on a television screen which is watched by a person using the system. The display is varied in accordance with the person's activity by monitoring a parameter of the user (pulse rate), and the speed of replay of the video record can vary as the pulse rate varies The rate itself can be part of the screen display.

BRIEF DESCRIPTION OF THE INVENTION

According to the present invention, there is provided video display apparatus for monitoring one or more parameters of a user and which consists of a pre-recorded audiovisual medium, apparatus for reproducing from the medium a composite audiovisual signal, and television display apparatus having an input for the said audiovisual signal and a screen display for viewing by the user, and wherein the apparatus includes, interposed between the reproduction apparatus and the television display apparatus, a signal modifying device which is adapted to modify the signal from the reproduction apparatus in such a fashion as to modify the screen display on the television display apparatus, such modification being dependent at least in part on a parameter of the user, and user parameter sensor apparatus for sensing a user parameter and adapted to feed a signal representative thereof to the signal modifying device, and characterised in that the pre-recorded audiovisual medium includes, in addition to the signal to be displayed on the screen, pre-recorded code signals and the signal modifying device includes means for detecting the pre-recorded code signals and modifying the output signal sent to the television display device in accordance therewith.

The term user parameter used herein is intended to encompass both conscious and unconscious input from the user. For example, the user parameter may be a psychophysiological parameter measured or sensed by suitable means. Alternatively, it may be an input such as pressure consciously applied to a suitable sensor such as a load cell, a rhythm tapped out on a keyboard with the fingers, or a sung musical note sensed by a microphone and suitable circuitry.

A particularly useful psychophysiological parameter is electrodermal activity, and in such a case the apparatus preferably includes a sensor responsive to electrodermal activity. It may conveniently be of the "wireless" type disclosed in International Publication WO93/02622.

The signal representative of a user parameter is one input to the signal modification unit. The other is the signal from the pre-recorded audiovisual material, which includes, in addition to the signal generating the display on screen, code signals for detection in the signal modification device, that device then modifying the output signal which passes to the television display apparatus in a fashion dependent upon the code signals detected. Preferably the code signals are recorded on the audiovisual recording medium as picture information in parts of the composite video signal which do not appear on the television display. Analogous techniques have been known for several years in television transmission technology and are used for so-called Teletext services. The signals embedded in appropriate code in the uppermost few lines of a picture (which are normally not visible on the screen but rather are blanked off) can be decoded by appropriate circuitry and used to generate a visual display. In practising the present invention, they can be decoded in similar fashion and used to control the appearance of the audiovisual signal output on the screen of the television apparatus.

The exact nature of the modification to the display of the video record on screen may vary widely. For example, the display may simply be overlain with a representation of the user parameter being sensed at the time, for example heartrate, together with a suitable scale, legend or the like. Such a display may vary in real time. Alternatively, the signal modification device may include means for capturing and analysing user parameter data over a period of time, e.g. the elapsed running time of the video recording, and then providing a display of some derived result therefrom.

In a further development, the signal modifying device may have provision for inputting a control signal, e.g. from a keyboard, keypad, joystick or other standard input device, as well as for inputting a user parameter, or more than one user parameter.

The preferred audiovisual recorded medium is a video recorded magnetic tape, most conveniently in pre-recorded video cassette form. Various video cassette formats and standards are known far various purposes and all of these can be used without difficulty. However, the preferred recorded medium for reasons of straightforward expense and availability is the standard video cassette used with a standard video cassette player. Such a player has a standard composite video output signal which can be simply connected as one of the inputs to the signal modifying device.

Alternative forms of medium can be used such as, for example, laser discs or interactive compact optical disc formats, but these are only materially useful when it is desired to do more than modify the display of the audio visual signal on the screen which is being viewed, for example, when it is desired to halt, slow or pause the reproduction of a continuous recording.

The signal modification device is preferably microprocessor controlled with the microprocessor having access to appropriately stored display data which can be selected in accordance with an appropriate predetermined programme and used to control the output video signal sent to the television apparatus. Commercially available microcontroller chips may be used. The precise way in which the display is varied by the device can vary very widely indeed. For example, the signal modification device may effectively superimpose a second image on the normal television screen image or it may, for example, blank out part of the image being sent from the reproducing apparatus and substitute for it an appropriate visual display.

Numerous variations may be made by simply re-programming the microprocessor controlling the signal modifying device. For example, the signal modifying device may be arranged to display on the screen an actual value, e.g. by the use of a variable height or variable length bar of a psychophysiological parameter of the subject being measured, for example electrodermal activity. Such a display may, if appropriate, include a graduated scale and absolutely sensed values may be displayed on the screen in an appropriate alphanumeric fashion.

In the use of the apparatus of the present invention for diagnostic purposes, it may be desired not to have the subject view the screen display as modified, but rather to provide two screen displays, one directly connected to the output of the reproduction device and the other connected via the signal modifying unit, that other being observed by a therapist or diagnostician who can then see changes in the psychophysiological or other parameters of the viewer of the pre-recorded material without the viewer of the pre-recorded material having such display.

By an appropriate combination of programming in the signal modification unit and pre-recorded signals on the audio visual pre-recorded medium, sophisticated biofeedback techniques may be developed. For example, the microprocessor-controlled signal modification unit may include a means not merely for constantly monitoring a signal representative of a psychophysiological parameter of a user, but means to record the changes over time. If, at the end of e.g. a suitably stimulating audiovisual record, the recorded medium contains an appropriate trigger signal, that trigger signal may be decoded in the signal modification unit to cause the television screen to display, e.g., a graph of stress against time over the period the subject was watching the stimulating audiovisual presentation.

The signal modification unit may, in accordance with the changes in the user parameter and/or other inputs such as cues on the recorded medium vary not only the visual display on the television screen, but also (or alternatively) the audio output.

Although the signal modification unit may be used simply to insert a static image over or substituting for part of the normally moving image displayed on the television screen, if the microprocessor has enough computing power, a superimposed image may be varied in time sufficiently quickly to appear animated.

BRIEF DESCRIPTION OF THE DRAWING

The present invention will be further illustrated by way of example with reference to a specific apparatus which is described in more detail below with reference to the accompanying drawings.

In the drawings.

DETAILED DESCRIPTION AND PRESENTLY PREFERRED EMBODIMENTS

Figure 1:
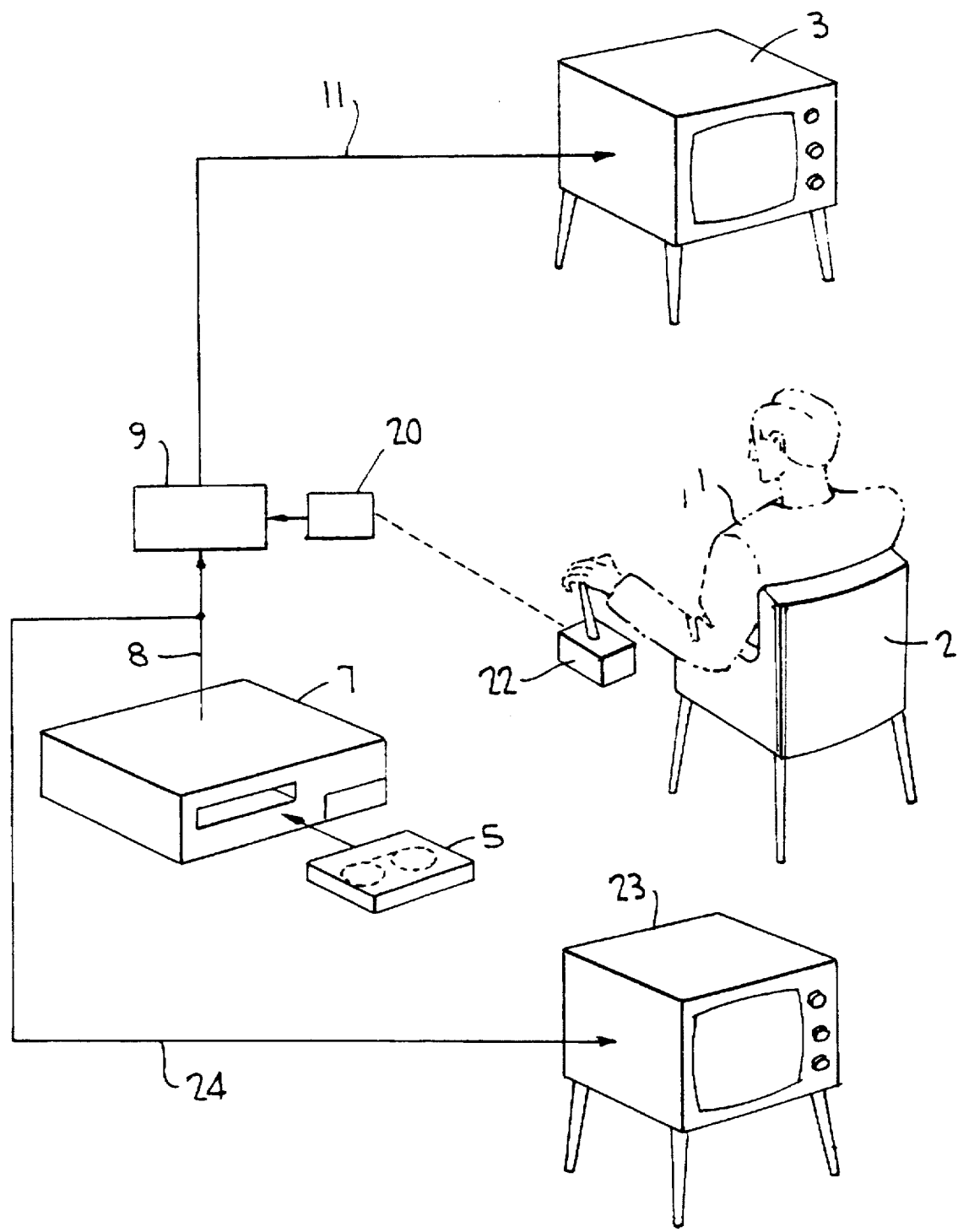
FIG. 1 is an overall diagram showing an apparatus of the present invention.

Referring first to FIG. 1 of the drawings, this shows diagrammatically a typical biofeedback arrangement using apparatus in accordance with the present invention. A user 1 seated in a chair 2 watches a television 3. The display on the television is basically that of a pre-recorded video cassette 5 which is inserted into a standard video cassette player 7, the output of which is fed by a conventional coaxial cable 8 to a signal modification unit 9.

The signal modification unit 9 has an output which is connected again by standard coaxial cable 11 to the input socket of the television 3.

The signal modification unit 9 has a second input from an infrared receiving unit 20 which picks up signals from an infrared transmitting unit 22 located adjacent the user's chair 2. The infrared transmitting unit 22 is arranged to emit a suitably modulated infrared signal, the modulation being dependent upon the electrodermal activity of the user 1, which is detected with the assistance of a pair of electrodes placed against two adjacent fingers on the user's left hand.

The system of generating for inputting into the signal modification unit 9 a signal representative of the electrodermal activity of the patient 1 may be analogous to that described in Specification WO93/02622.

Figure 2:
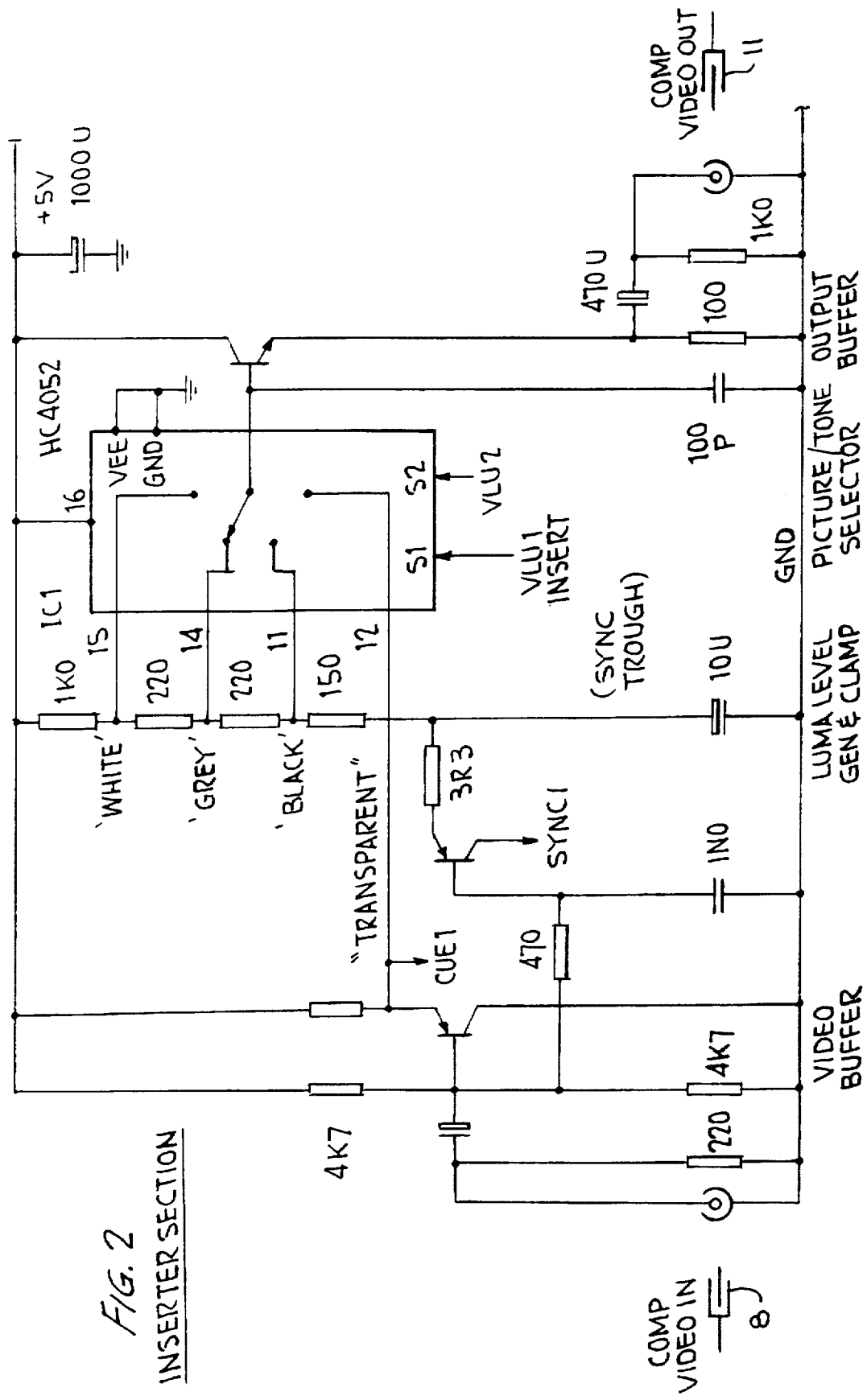
FIG. 2 is a practical circuit diagram for one part of the signal modification unit and FIG. 3 is a circuit diagram of a separate part of the signal modification unit adapted to operate in conjunction with the part shown in FIG. 2.
Figure 3:
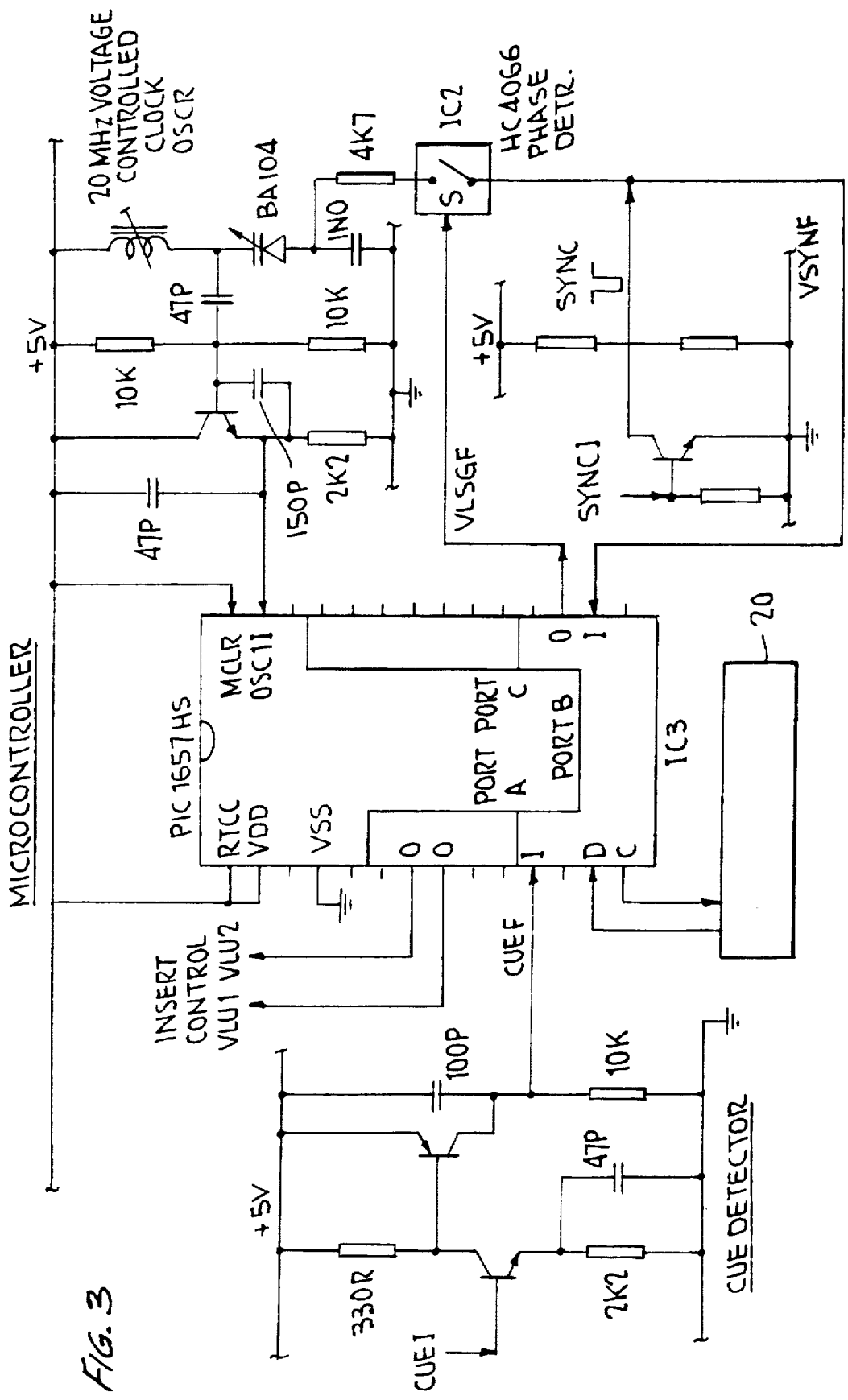

Within the casing of signal modification unit 9 are located appropriate circuit modules, power supplies, etc. to provide the desired effect. FIGS. 2 and 3 show certain parts of the circuitry and attention is fist of all directed to FIG. 2 which may be thought of as the inserter section of the circuit. As can be seen, it has a composite video signal coaxial input socket on the left for coaxial cable 8 and a composite video output socket on the right into which the coaxial cable 11 is inserted in use.

The circuit of FIG. 2 shows as indicated four basic sections, viz. a video buffer section from which a cue I signal is derived, a luminous level generator and clamp section, a picture/tone selector section and an output buffer.

The separate important section of the signal modification unit 9 is shown in FIG. 3 and as can be seen, this is basically built around a central microprocessor unit, in the example illustrated a microcontroller type PIC16C57HS.

Connected to this microprocessor is the wireless receiver 20 which receives the modulated infrared from transmitter 22, a cue detector circuit having as input the cue I output signal shown in FIG. 2, a voltage controlled oscillator section and a sync separator section. The microprocessor unit has two outputs identified as VLU1 and VLU2 which are fed to the picture/tone selector, in the example illustrated an integrated circuit type HC4052, shown in FIG. 2.

In operation, the single chip microcontroller type PIC16C57HS, which is fed from the sync separator circuit shown at the bottom right of FIG. 3, carries out all the timing and insertion control output drive operations which are necessary to insert luminance signals into appropriate raster lines of the outgoing composite picture signal.

In order to ensure steadiness of the picture viewed, it is desirable to lock the microcontroller clock to the incoming video signal. The voltage controlled clock oscillator shown at the top right of FIG. 3 is fed with a signal from a phase detector which compares the timing of the pulses from the sync separator circuit against gating pulses emitted from a microcontroller output in port B thereof.

Stored within the microcontroller are appropriate digital data to enable an appropriate waveform to be generated which is superimposed on the outgoing signal in coaxial cable 11. For example, the data may correspond to bar indicators, graph or histogram axes and standard text characters, all of which may be displayable on the screen of television 3 in accordance with the programming within the microcontroller.

The microcontroller has two outputs identified as VLU1 and VLU2 and these serve as inputs to the picture/tone selector chip type HC4052 forming part of the inserter section shown in FIG. 2.

As the video cassette 5 is played, cue commands in the composite signal may be extracted by the video buffer circuit and detected by the cue detector circuit shown in FIG. 3. Cue signals may be, for example, on-off coded sequences of blue phase luminance only signal recorded on raster lines which lie outside the normal screen area. The cue detector is a simple high frequency detector feeding an input on port B of the microcontroller.

Not shown in the drawing is that the microcontroller may have a further output leading to an audio gate circuit to enable the sound signals to be controlled. If desired, the microcontroller may generate its own sound signals and overlay these on the sound signals already present in the video composite signal. Again, this is not shown in the drawings. FIG. 1 does, however, show a second screen display 23 connected directly to video cassette player 7 via a lead 24, for observation by a therapist or diagnostician as set forth above.

As can be seen, the operation of the signal modification unit is essentially controlled by the microcontroller which must, of course, be programmed in appropriate fashion to operate properly. For example, it should be arranged continuously to monitor and detect the incoming field sync pulse in the composite video signal at VSYNF. This is input to the microcontroller at one of the inputs in port B. The programming is arranged so that a two microsecond pulse is output likewise via port B as indicated at VLSGF. This output two microsecond pulse will be centred on the expected position of the trailing edge of the incoming line sync pulse. The microcontroller is arranged to monitor the synchronisation lock or loss of such locking from the timing at VSYNF.

The microcontroller is also arranged to detect a line sync pulse preceding lines 6 or 318 of the successor frames of the composite video signal and then to read and decode any cue signals which appear on lines 24 to 26 and 337 to 338.

Following the decoding of any cue signals which are present, these may cause the microcontroller to select appropriate data from memory and to use that date to provide a signal on one or both of outputs VLU1, VLU2.

Other details of the two circuit sections are indicated on the drawings.

The circuit illustrated in FIGS. 2 and 3 is, as can be seen, relatively simple and makes use extensively of the sophistication available with a programmable microcontroller. These are available inexpensively even with the necessary performance to handle the rapidly flowing input signals. The microcontroller carries out all of the timing and insertion control output drive operations which are necessary to insert appropriate luminance signals into the parts of the composite video signal which correspond to parts of the screen of the television which are viewed by the user 1.

We claim:

1. Video display apparatus for monitoring one or more user parameters of a user, the apparatus comprising:
    a television display apparatus having an input for an audiovisual signal and a screen display for viewing by the user;
    a pre-recorded audiovisual medium having contained thereon a signal to be displayed on said screen display and at least one pre-recorded code signal;
    a reproduction apparatus for reproducing from said medium a composite audiovisual signal;
    a user parameter sensor apparatus for sensing electrodermal activity of a user and generating a signal representative of said electrodermal activity;
    a signal modifying device connected to and interposed between said reproduction apparatus, said television display apparatus, and said user parameter sensor apparatus, the signal modifying device further having a means for detecting said at least one pre-recorded code signal and a means for modifying an output signal sent to the television display device by the insertion of an image over at least part of said screen display, said image being dependent on said signal from said parameter sensor apparatus in combination with said at least one pre-recorded code signal; and
    a screen display modifier for deleting part of the image on said screen display wherein the part of the image deleted is responsive to said signal from said parameter sensor apparatus in combination with said at least one pre-recorded code signal.

2. Apparatus according to claim 1, wherein said at least one pre-recorded code signal is recorded as part of a recorded composite video signal with said at least one pre-recorded code signal being embedded on raster lines not normally shown on the standard television display device.

3. Apparatus according to claim 1 wherein the user parameter sensor apparatus and the signal modifying device are connected one to another in wireless fashion.

4. Apparatus according to claim 1 further comprising at least one additional signal input means connected to the signal modifying device.

5. Apparatus according to claim 1 wherein the pre-recorded audiovisual medium is a video cassette.

6. Apparatus according to claim 1 further comprising an additional television display apparatus having a screen arranged to display thereon the unmodified composite audiovisual signal emerging from the reproduction apparatus.

7. Apparatus according to claim 1 wherein the television display apparatus provides acoustic output and wherein the signal modifying device modifies the acoustic output from the television display apparatus.

8. Apparatus according to claim 1 wherein the signal modifying device is controlled by a microprocessor and, by a combination of programming therein and the at least one pre-recorded code signal, analyzes variations in the user parameter over time and then modifies the screen display in dependence on such analysis.

9. Apparatus according to claim 1 wherein the signal modifying device decodes said at least one pre-recorded code signal on the recording medium and displays a representation of the user parameter being sensed at the time in dependence on said at least one pre-recorded signal.

10. Apparatus according to claim 1 wherein the image inserted over at least part of the screen display is superposed over a part of the image blanked out on the screen display.

11. Apparatus according to claim 10 wherein the image inserted is representative of a user parameter sensed.

* * * * *